US006032668A

United States Patent [19]

Chung

[11] Patent Number: 6,032,668

[45] Date of Patent: Mar. 7, 2000

[54] FIRE EMERGENCY LIFE SAVING ARRANGEMENT

[76] Inventor: Chao Yang Chung, 5F, 116-4, Ching Chung Chieh, Chien Chen Chiu, Kaohsiung Ciry, Taiwan

[21] Appl. No.: 09/072,578

[22] Filed: May 4, 1998

[51] Int. Cl.[7] .......... A61M 16/00; A62B 7/00; A62B 18/08

[52] U.S. Cl. .......... 128/206.27; 128/204.18; 128/205.22; 206/803

[58] Field of Search .......... 128/204.18, 205.22, 128/205.27, 200.24, 206.27; 206/803

[56] References Cited

U.S. PATENT DOCUMENTS

| | | | |
|---|---|---|---|
| 2,450,610 | 10/1948 | Pierce | 128/204.18 |
| 2,831,607 | 4/1958 | Berndt | 128/204.18 |
| 4,640,278 | 2/1987 | Barry | 128/206.12 |
| 4,802,472 | 2/1989 | Jung | 128/204.18 |
| 5,003,974 | 4/1991 | Mou | 128/205.27 |
| 5,113,854 | 5/1992 | Dosch et al. | 128/205.27 |
| 5,165,395 | 11/1992 | Ricci | 128/202.22 |
| 5,461,934 | 10/1995 | Budd | 128/204.18 |
| 5,676,135 | 10/1997 | McClean | 128/205.22 |
| 5,746,492 | 5/1998 | Tai | 362/20 |

*Primary Examiner*—John G. Weiss
*Assistant Examiner*—Todd Martin
*Attorney, Agent, or Firm*—Raymond Y. Chan; David and Raymond

[57] ABSTRACT

A fire emergency life saving arrangement includes an air storage area, a buffer air area, a face cover storage area, and an electrical area, wherein the air storage area includes an end wall having an uni-directional air pumping valve, and a releasing valve between the air storage area and the buffer air area. The face cover storage area provides a face cover. A predetermined location on a front end of the face cover is integrally extended a telescopic pipe. Another end of the telescopic pipe is connected to an air hole provided on a first dividing plate of the buffer air area so that clean air can travel from the buffer air area through the telescopic pipe to the face cover of the user and allow the user to receive clean air once the releasing valve is pressed down. A microphone is installed near an opening of the telescopic pipe on the face cover. The electrical area contains a lighting set, a speaker, and a circuitry control unit for providing electricity right after the electric charging is ceased. The above disclosed structure allows the user to operate the fire emergency life saving arrangement in a short time to receive clean air, adequate lighting, and send out a loud SOS emergency signal to the rescuer to help the user to escape from a burning building.

20 Claims, 5 Drawing Sheets

FIRE EMERGENCY LIFE SAVING ARRANGEMENT

FIELD OF THE PRESENT INVENTION

The present invention relates to a fire emergency life saving arrangement. More particularly to a life saving kit that provides clean air, adequate lighting, and a loud emergency signal to rescuers during a building fire.

BACKGROUND OF THE PRESENT INVENTION

No one can predict the time and the location of a building fire, but everyone knows how terrifying and devastating a building fire can be. In a building fire, the out of control fire not only destroys property, but also takes away precious human life. Thus, whether in the public or private sector, people have worked hard to improve both how to prevent fires and how to react during a fire to save lives. People have worked hard to try to minimize property damage and the loss of human life.

From many years of researching building fires, the inventor learned that during a building fire, the resulting heat, smoke, and often loss of power causes people to quickly panic. Panic arises when the building loses electrical power plunging rooms into total darkness, smoke fills the air, and the intense heat of the fire quickly raises building temperatures. Once a building fire occurs, the first three minutes is the best time for people to escape from the building. After the first three minutes, a person's chance for escape from a building fire decreases with each passing second, because the building is either totally filled up with heavy smoke or the fire is already burning out of control. After the first three minutes, it may be too late for people trapped in the burning building. People still trapped in a burning building might not be able to escape and eventually lose their lives.

Although conventional fire emergency life saving apparatus may provide oxygen and provide emergency lighting, during a building fire most people fail to operate the oxygen supply for the first time, under a panic situation. During such a situation, a person cannot afford to make a mistake, simply because it is a life and death situation. Each second the person saves and each additional breath the person takes can make a big difference. The conventional fire emergency escape arrangement does not provide such user friendly simple procedure, that is why the result of saving life is still in need of much improvement.

SUMMARY OF THE PRESENT INVENTION

The main objective of the present invention is to provide a fire emergency life saving arrangement that provides enough clean air, adequate lighting, and a distinctive emergency sound to attract rescuers during a building fire, wherein the fire emergency life saving arrangement is a user friendly device, increasing a person's chance of escaping from a burning building.

Another objective of the present invention is to provide a fire emergency life saving arrangement, which is designed to be in an arch shape container, wherein the arch shape is perfectly fitted to a waist section of human body. It is shaped so that people can fasten the fire emergency life saving arrangement of the present invention on his or her waist area by a belt provided on the container during the building fire.

Accordingly, a fire emergency life saving arrangement comprises an arch container body having a first dividing plate vertically separating the arch container body into a large area and a small area; a second dividing plate further horizontally separating the large area into an air storage area and a buffer air area; and a third dividing plate further horizontally separating the small area into a face cover storage area and an electrical area. The air storage area of the arch container body further comprises an end wall having an uni-directional air pumping valve for filling air into the air storage area; and a tapered air hole provided on the second dividing plate of the air storage area that gradually tapers off from the air storage area towards the buffer air area. The arch container body further has a releasing hole in alignment with the tapered air hole of the second dividing plate of the air storage area; the releasing hole has a releasing rod of a releasing valve that passes therethrough. The releasing valve further comprises a pressing button, a cushion and a plug, wherein the pressing button and the cushion are attached on a top end of the releasing rod, and the plug is attached to a bottom end of the releasing rod. The plug is constructed to fittingly plug the tapered air hole of the second dividing plate of the air storage area when not in use. During an emergency situation, the user can press down the pressing button of the releasing valve and push the releasing rod downwardly so that the tapered air hole of the second dividing plate is no longer blocked by the plug and clean air that was originally stored within the air storage area can be released into the buffer air area. Furthermore, on the first dividing plate facing the buffer air area, an air hole is extended through the first dividing wall for allowing clean air to travel from the buffer air area through a telescopic pipe to a face cover stored in the face cover storage area. The face cover is folded in half and stored therein. The telescopic pipe is integrally extended from a predetermined location on a front end of the face cover to the first dividing wall. The face cover further comprises two flexible fastening belts for wrapping around a head portion of the user. A microphone is installed on the face cover near an opening of the telescopic pipe. On a front wall of the face cover storage room has a cover, and on the cover, a pull out handle is integrally attached for the user to open the face cover storage area by pulling the pull out handle and thereby pulling off the cover. The third dividing plate has provided a wire hole. The adjoining electrical area has installed a lighting set, a speaker, and a circuitry control unit for providing electricity right after an electricity charging is ceased. The circuitry control unit has integrally connected an electrical wire and a cable wire. The electrical wire passes through the wire hole of the third dividing plate and the telescopic pipe to integrally connect with the microphone. The cable wire has a plug at one end that is integrally connected to the socket plug to provide the circuitry control unit with an electrical charge when the plug connects to the socket plug. The plug is connected to the socket plug when the arrangement is not being used, thereby providing the circuitry control unit with an electrical charge. The arrangement is then in an electrical charge mode.

DETAILED DESCRIPTION OF THE PREFERRED EMBODIMENT

Figure 1:
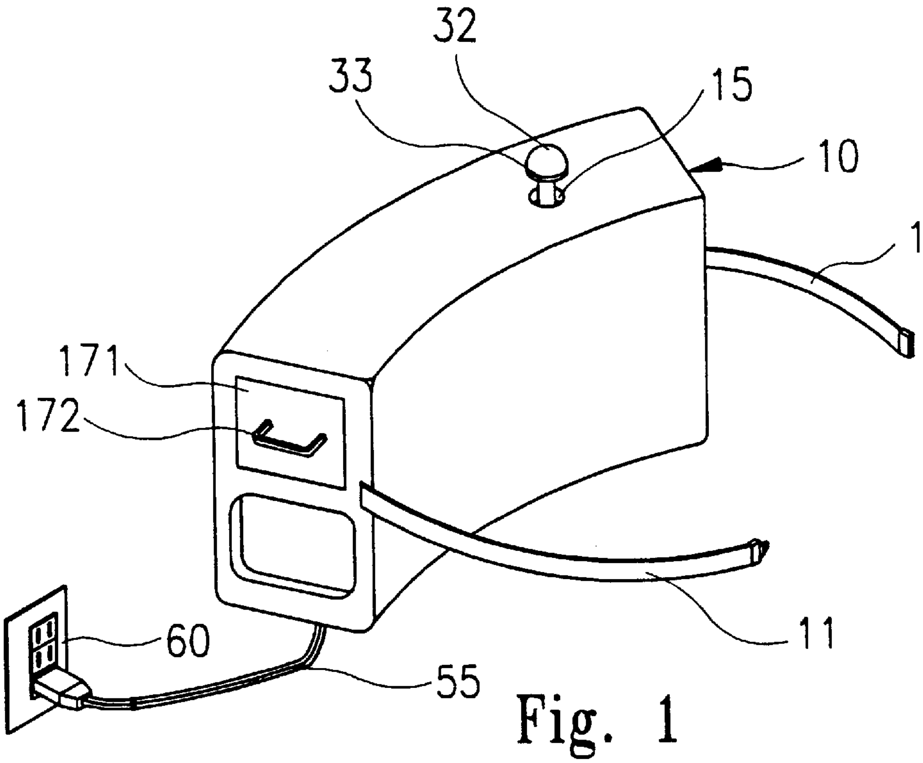
FIG. 1 is a perspective view of a fire emergency life saving arrangement according to a first preferred embodiment of the present invention.
Figure 2:
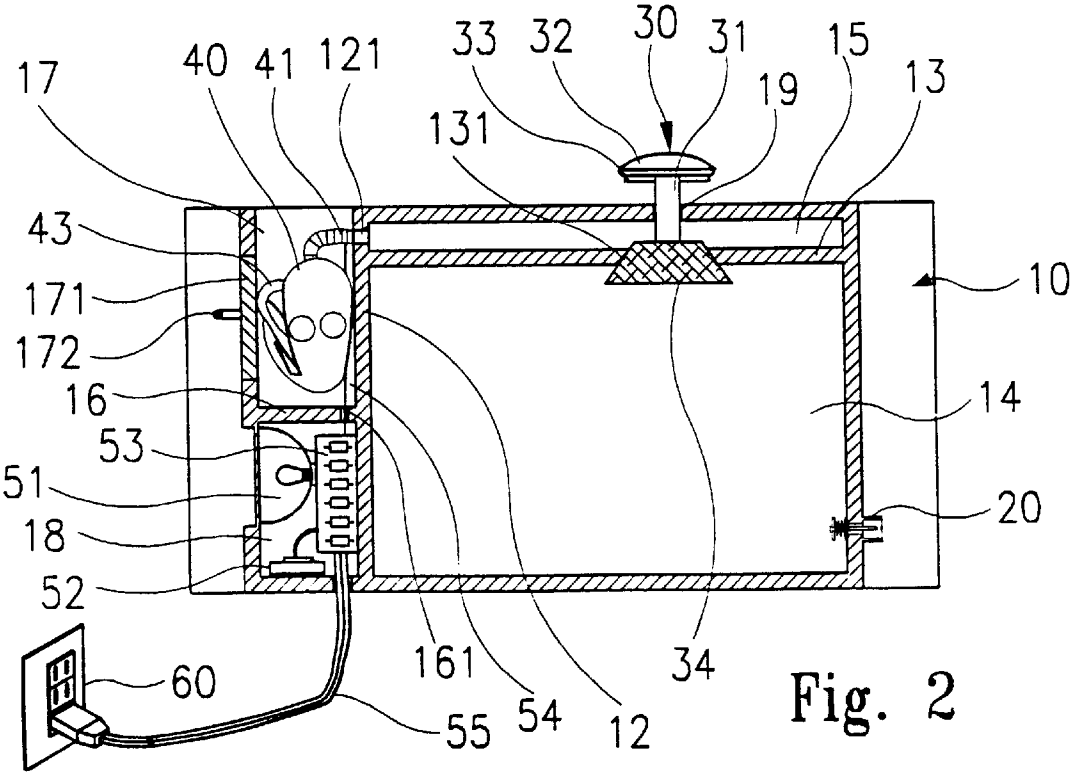
FIG. 2 is a sectional view of the fire emergency life saving arrangement according to the above first preferred embodiment of the present invention.
Figure 3:
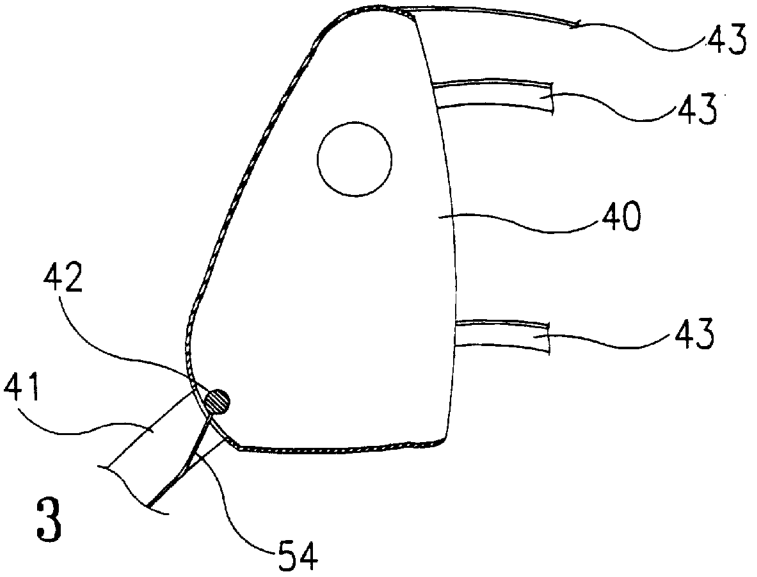
FIG. 3 is a sectional view of a face cover according to the above first preferred embodiment of the present invention.

Referring to FIGS. 1 to 3 of the drawings, a fire emergency life saving arrangement according to a first preferred embodiment of the present invention is illustrated. The fire emergency life saving arrangement of the present invention comprises an arch container body 10 having a first dividing plate 12 vertically separating the arch container body 10 into a large area and a small area, a second dividing plate 13 further horizontally separating the large area into an air storage area 14 and a buffer air area 15, a third dividing plate 16 further horizontally separating the small area into a face cover storage area 17 and an electrical area 18. The air storage area 14 of the arch container body 10 further comprises an end wall having an uni-directional air pumping valve 20 installed thereon for filling air into the air storage area 14. The second dividing plate 13 of the air storage area 14 provides a tapered air hole 131 thereon that gradually tapers off from the air storage area 14 towards the buffer air area 15. The arch container body 10 further has a releasing hole 19 in alignment with the tapered air hole 131 of the second dividing plate 13 of the air storage area 14. A releasing rod 31 of a releasing valve 30 passes through the releasing hole 19. The releasing valve 30 further comprises a pressing button 32, a cushion 33 and a plug 34, wherein the pressing button 32 and the cushion 33 are mounted on a top end of the releasing rod 31 and the plug 34 is affixed to a bottom end of the releasing rod 31. The plug 34 is constructed to fittingly plug the tapered air hole 131 of the second dividing plate 13 of the air storage area 14. During an emergency situation, the user can press down the pressing button 32 to push the releasing rod 31 downwardly so that the tapered air hole 131 of the second dividing plate 13 is no longer blocked by the plug 34 and clean air that was originally stored within the air storage area 14 can release into the buffer air area 15. Furthermore, on the first dividing plate 12 facing the buffer air area 15, an air hole 121 is provided extending through the first dividing plate 12 for allowing air to travel from the buffer air area 15 through a telescopic pipe 41 to a face cover 40 which is folded and stored in the face cover storage area 17. The telescopic pipe 41 has one end connected to the air hole 121 and another end connected to a front end of the face cover. The face cover 40 further comprises two flexible fastening belts 43 extended therefrom for wrapping around the head portion of the user to protect the face of the user including eyes, noise, and mouth from smoke, as shown in FIG. 3. A microphone 42 is installed on the face cover 40 near an opening of the telescopic pipe 41.

A cover 171 is provided on a front wall of the face cover storage area 17 which has a pull out handle 172 affixed thereon for the user to open the face cover storage area 17 by pulling the pull out handle 172 and thereby pulling off the cover 171. The third dividing plate 16 has a wire hole 161. The adjoining electrical area 18 contains a lighting set 51 attached thereon, a speaker 52 and a circuitry control unit 53 for providing electricity right after an electricity charging is ceased. The circuitry control unit 53 electrically connects an electrical wire 54 and a cable wire 55, wherein the electrical wire 54 passes through the wire hole 161 of the third dividing plate 16 and the telescopic pipe 41 to integrally connect with the microphone 42, and the cable wire 55 has a plug connected for plugging in an electrical socket 60 in order to charge the circuitry control unit 53. The plug is electrically connected with the socket 60 when the arrangement is not in used, thereby providing the circuitry control unit 53 with an electrical charge. The arrangement is then in an electrical charge mode. During an emergency situation, if the cable wire 55 is disconnected from the socket 60 or the electricity supply of the socket 60 is ceased, the circuitry control unit 53 would then supply electricity to the microphone 42 and lighting set 51.

Referring to FIG. 2 of the drawings, when the present invention is in a ready to use stage, the cable wire 55 is plugged into the socket 60, and the air storage area 14 has adequate clean air pumped in from the outside through the uni-directional air pumping valve 20. During a regular routine check, the user can disconnect the cable wire 55 from the socket 60, to see if the lighting set 51 provides adequate lighting or if the circuitry control unit 53 is working properly to provide electricity. The user also needs to check the air pressure in the air storage area 14 by using any pressure meter (such as the tire pressure meter) to check the pressure from the uni-directional air pumping valve 20. If the air pressure is too low, the operator can use a regular air pump to fill up the air storage area 14.

Figure 4:
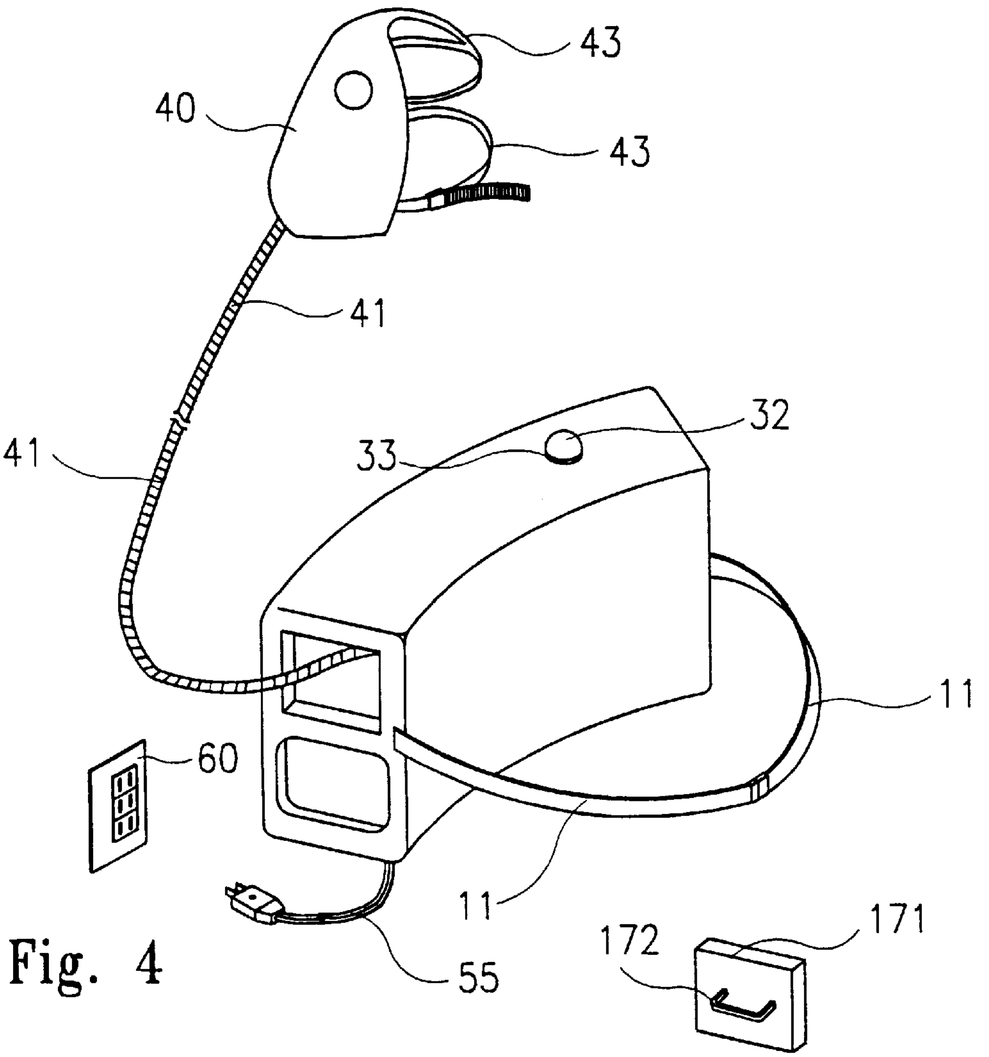
FIG. 4 is a perspective view of the fire emergency life saving arrangement during operation according to the above first preferred embodiment of the present invention.
Figure 5:
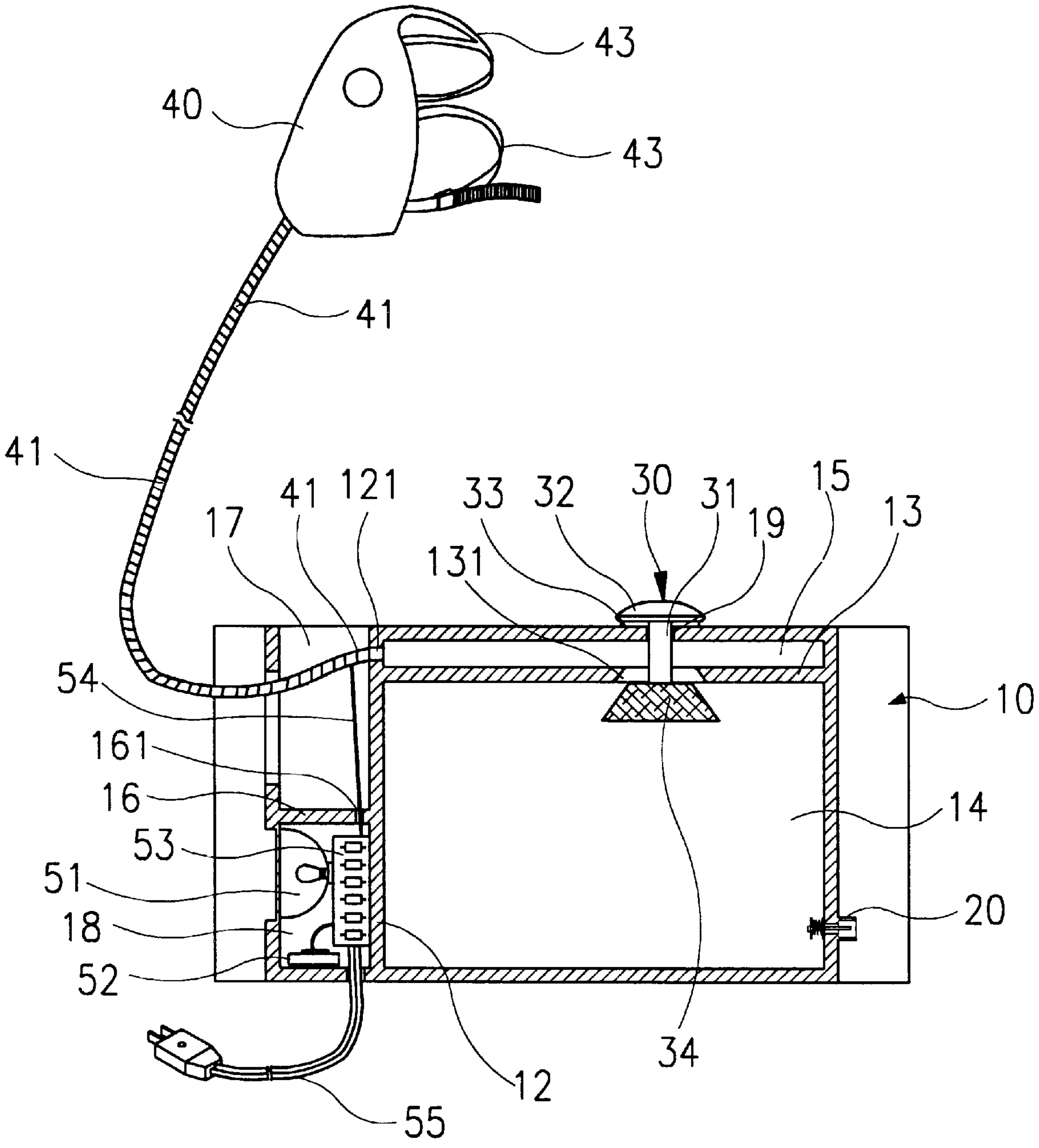
FIG. 5 is a sectional view of the fire emergency life saving arrangement during operation according to the above first preferred embodiment of the present invention.

Referring to FIGS. 4 and 5 of the drawings, when the user is in a building fire and needs to use the fire emergency life saving arrangement of present invention to save his or her life, the user must first remove the plug of the cable wire 55 from the socket 60. If the electricity has already been cut off due to the fire, the arrangement's lighting set 51 will automatically turn on. Once electricity ceases flowing from the external power source through the cable wire 55, the circuitry control unit 53 should instantly provide electricity to the lighting set 51 to provide adequate lighting. If the electrical power of the building has been cut off because of the fire, the lighting provided by the fire emergency life saving arrangement of the present invention can give the user a quick awareness of his surroundings and a sense of direction, so that he or she can best decide how to escape from the building fire. After disconnecting the plug of the cable wire 55, the user can fasten the arch container body 10 of the fire emergency life saving arrangement around his waist section by two belts 11 connected to the two sides of the arch container body 10. The user can immediately pull the pull out handle 172 to remove the cover 171 of the face cover storage area 17, so that the user can take out the face cover 40 from the face cover storage area 17 and fasten the face cover 40 on the head portion by the fastening belt 43 so as to protect the eyes, noise, and mouth of the user from the smoke generated by the building fire. The user may then press down the pressing button 32 of the releasing valve 30 to allow the flow of clean air from the air storage room 14 through the buffer air area 15, the air hole 121 of the first dividing plate 12 and the telescopic pipe 41 to deliver clean air to the face cover 40 for the user to breathe. From the above disclosure of the present invention, it is apparent that the operation process of the present invention consists of only a few simple steps. Therefore, in case of a building fire, even under a panic situation, with the help of the present invention, the user can quickly identify his or her location and escape the building fire with his or her face well protected from heavy smoke by the face cover 40.

Figure 6:
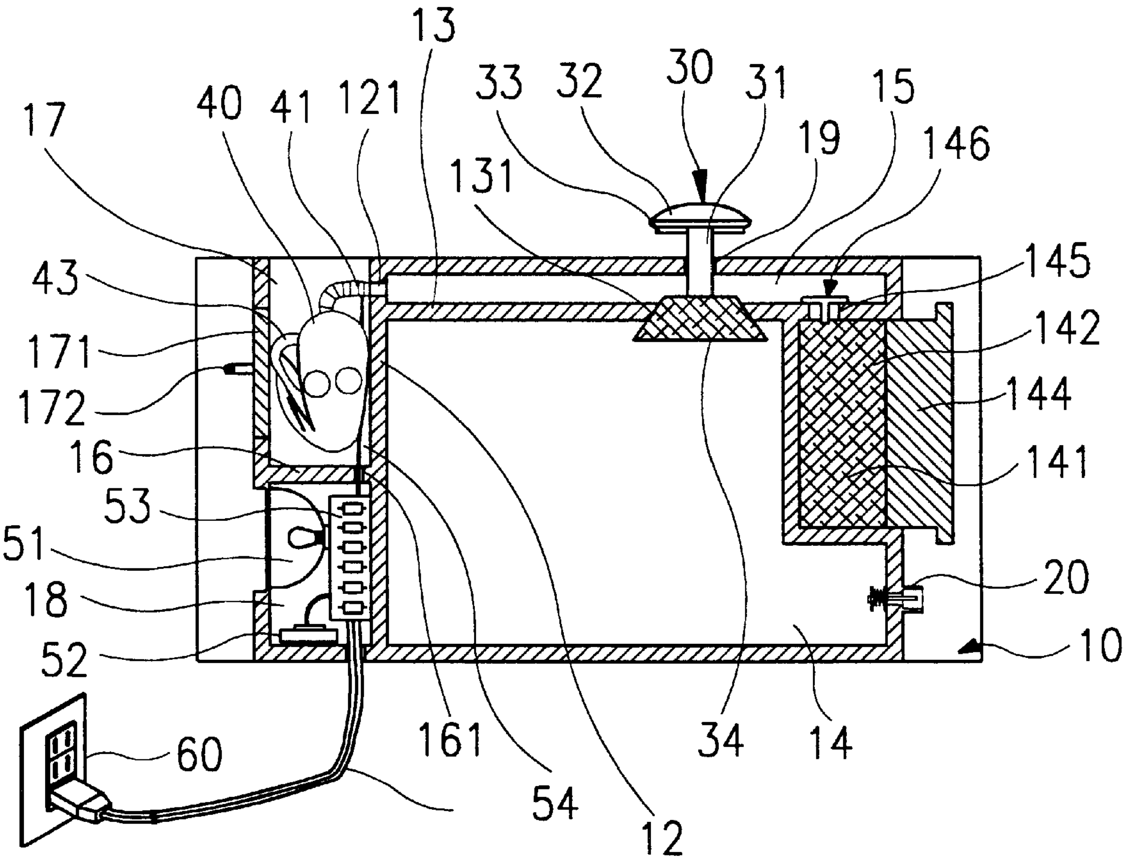
FIG. 6 is a sectional view of the fire emergency life saving arrangement according to a second preferred embodiment of the present invention.
Figure 7:
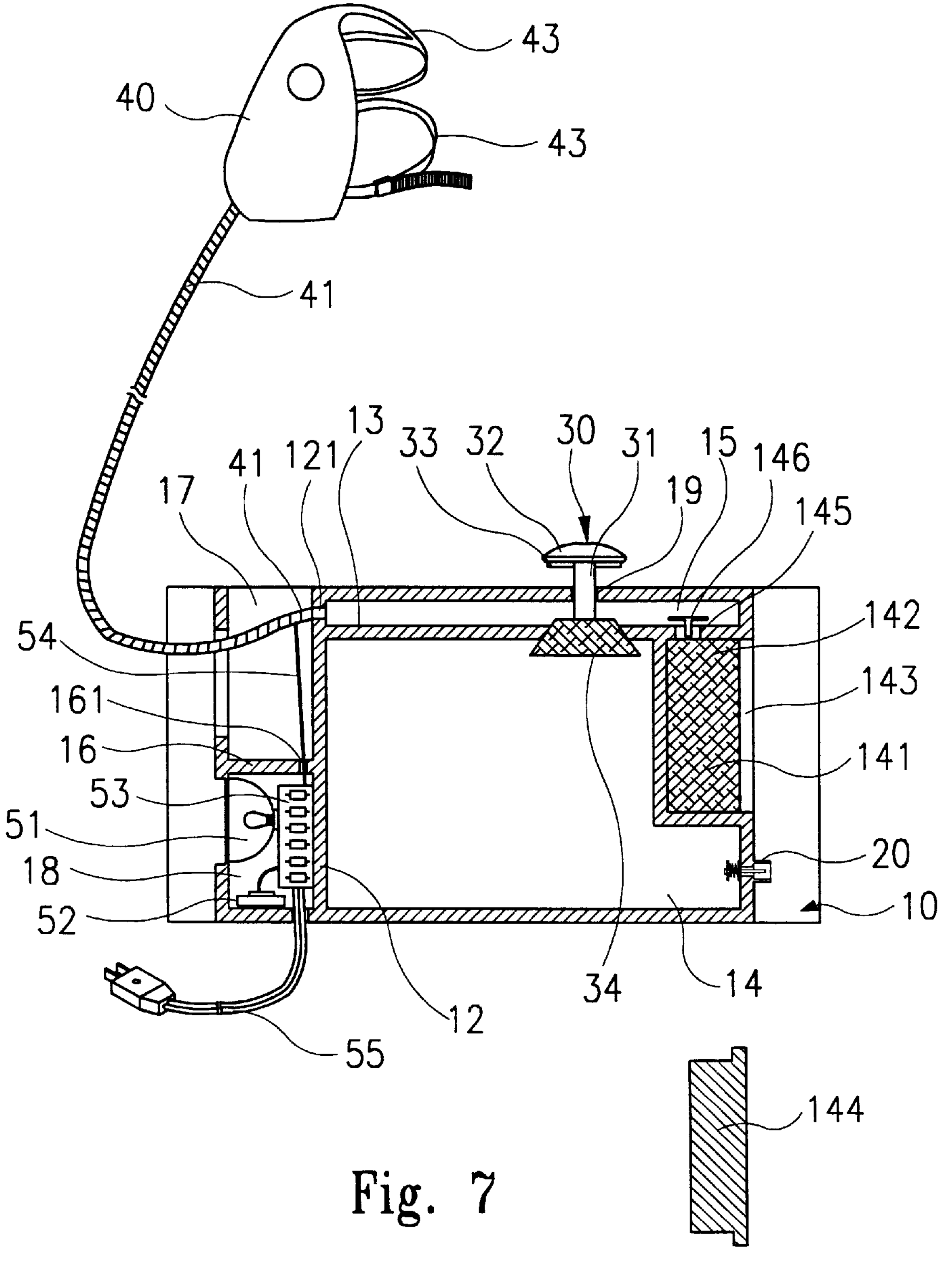
FIG. 7 is a sectional view of the fire emergency life saving arrangement during operation according to the above second preferred embodiment of the present invention.

Referring to FIGS. 6 and 7 of the drawings, a fire emergency life saving arrangement according to a second preferred embodiment of the present invention is illustrated, which further comprises an air filtering area 141 between the second dividing plate 13 and the end wall of the air storage area 14. The air filtering area 141 contains a filter 142 (such as active carbon) installed therein, and has an air intake opening 143 provided on a wall of the filtering area 141 for allowing dirty air to enter. A side cover 144 which is attached on the air intake opening 143 is used to cover the air intake opening 143. On the second dividing plate 13, an air outlet hole 145 is provided for the buffer air area 15 communicating with the air filtering area 141. An air outlet valve 146 is used to close the air outlet hole 145. Therefore, during the early stage of a building fire, the user can merely pull out the side cover 144 to allow the slightly smoky air to enter the air filtering room 143 through the air intake opening. After the filter 142 has filtered the smoky air, the filtered air flows into the buffer air area 15 through the air outlet valve 146. The air in the buffer air area 15 may flow through the telescopic pipe 41 to the face cover 40 for the user to breathe. After the building has been burning for a while, when the air in the building fire becomes too thin, the user can then press down the releasing valve 30 to receive clean air stored in the air storage area 14.

Accordingly, the present invention can substantially achieve at least the following advantages:

1. Many life saving functions: The fire emergency life saving arrangement of the present invention not only has all the functions of the conventional fire-related emergency escape apparatus, but also has an additional function over the prior art. That is the fire emergency life saving arrangement is able to send out a loud SOS emergency signal to rescuers through the speaker, so that rescuers can more easily locate the user trapped in the building fire. The user can also use the speaker to communicate with other people trapped in the building fire in order to help each other to get out of the fire. Also, another important improvement of the present invention is that the lighting set can provide adequate lighting right after the electricity is been cut off, so that the user can easily locate the fire emergency life saving arrangement of the present invention and see the surroundings to find the best route to exit the burning building.

2. Simplicity: The operation process of the present invention is very simple. During a fire, the user merely needs to unplug the plug of the cable wire form the socket, to open the face cover storage room and apply the face cover to protect the face section of the user, and then to press down the pressing button on the arch container body. The user can instantly be fed with clean air. Moreover, the arrangement of the present invention also provides adequate lighting and a microphone which is capable of sending out a loud SOS emergency signal to rescuers. The whole operation process can be completed in seconds.

3. High safety: Due to the fact that, right after the user has the present invention in hand, the user has adequate lighting available to assist him or her to locate the face cover, and immediately knows where he or she is located in the burning building. The face cover of the present invention is for covering the whole face section (including eyes, nose, and mouth of the user) unlike the conventional face cover which only covers the nose and mouth, leaving the user's eyes exposed to smoke, causing irritation and hindering escape. Furthermore, the present invention provides normal clean air, eliminating the danger of the oxygen tank.

4. Lightweight: The conventional fire emergency escape apparatus used oxygen as the source of air, wherein the oxygen tank used to carry the oxygen is relatively heavier than the present invention. The arch container body of the present invention is used for only storing normal air, so that it is much lighter in weight, and thus would not hinder the escape from the building fire.

What is claimed is:

1. A fire emergency life saving arrangement, comprising a container body which is separated into a large area and a small area by a first dividing plate, wherein said large area is separated into an air storage area for storing a predetermined amount of clean air and a buffer air area by a second dividing plate, and said small area has a face cover storage area, wherein said air storage area comprises and end wall having an uni-directional air pumping valve installed thereon for filling air into said air storage area, said second dividing plate positioned between said air storage area and said buffer air area having a tapered air hole thereon that gradually tapers off from said air storage area towards said buffer air area, said container body further having a releasing hole which is provided on an outer wall thereof and positioned in alignment with said tapered air hole, furthermore, on said first dividing plate facing said buffer air area, an air hole is provided extending though said first dividing plate;

a releasing valve which comprises a releasing rod passing through said releasing hole, a pressing button and a cushion mounted on a top end of said releasing rod, and a plug hole, a pressing button and a cushion mounted on a top end of said of said releasing rod, and a plug affixing to a bottom end of said releasing rod, wherein said plug is constructed to fittingly shut off said tapered air hole of said dividing plate of said air storage area, therefore during an emergency situation, said pressing button is able to be pressed down to push said releasing rod downwardly so that said tapered air hole is no longer blocked by said plug and said clean air that was originally stored within said air storage area releases into said buffer air area; and a telescopic pipe having a first end connected to said air hole on said first dividing plate and a second end connected to a face cover storing in said face cover storage area wherein said air hole allows said clean air to travel from said buffer air area through said telescopic pipe to said face cover.

2. A fire emergency life saving arrangement, as recited in claim 1, wherein said face cover further comprises at least one flexible fastening belt extended therefrom for wrapping around a head portion of a user to protect eyes, noise, and mouth of said user.

3. A fire emergency life saving arrangement, as recited in claim 1, further comprising a microphone which is installed on said face cover near said second end of said telescopic pipe.

4. A fire emergency life saving arrangement, as recited in claim 2, further comprising a microphone which is installed on said face cover near said second end of said telescopic pipe.

5. A fire emergency life saving arrangement, as recited in claim 1, further comprising a cover which is provided on a front wall of said face cover storage area which has a pull out handle affixed thereon for said user to open said face cover storage area by pulling said pull out handle and thereby pulling off said cover.

6. A fire emergency life saving arrangement, as recited in claim 4, further comprising a cover which is provided on a front wall of said face cover storage area which has a pull out handle affixed thereon for said user to open said face cover storage room by pulling said pull out handle and thereby pulling off said cover.

7. A fire emergency life saving arrangement, as recited in claim 1, wherein said small area is separated into said face cover storage area and an electrical area by a third dividing plate which has a wire hole, said electrical room containing a lighting set attached thereon, a speaker and a circuitry control unit for providing sound signals and electricity to said lighting set right after an electricity charging of said circuitry control unit is ceased, said circuitry control unit electrically connecting an electrical wire and a cable wire, wherein said electrical wire passes through said wire hole of said third dividing plate and said telescopic pipe to integrally connect with said microphone, and said cable wire has a plug connected for connecting with an electrical power supply source in order to charge said circuitry control unit, thereby said plug is electrically connected with said electrical power supply source for providing said circuitry control unit with an electrical charge when said fire emergency life saving arrangement is not in used, however during an emergency situation, when said cable wire is disconnected from said electrical power supply source or said electricity supply of said electrical power supply is ceased, said circuitry control unit immediately supplies electricity to said lighting set.

8. A fire emergency life saving arrangement, as recited in claim 6, wherein said small area is separated into said face cover storage area and an electrical area by a third dividing plate which has a wire hole, said electrical room containing a lighting set attached thereon, a speaker and a circuitry control unit for providing sound signals and electricity to said lighting set right after an electricity charging of said circuitry control unit is ceased, said circuitry control unit electrically connecting an electrical wire and a cable wire, wherein said electrical wire passes through said wire hole of said third dividing plate and said telescopic pipe to integrally connect with said microphone, and said cable wire has a plug connected for connecting with an electrical power supply source in order to charge said circuitry control unit, thereby said plug is electrically connected with said electrical power supply source for providing said circuitry control unit with an electrical charge when said fire emergency life saving arrangement is not in used, however during an emergency situation, when said cable wire is disconnected from said electrical power supply source or said electricity supply of said electrical power supply is ceased, said circuitry control unit immediately supplies electricity to said microphone and lighting set.

9. A fire emergency life saving arrangement, as recited in claim 1, furthering comprising at least one belt connected to said container body for fastening said container body around a waist section of a user.

10. A fire emergency life saving arrangement, as recited in claim 8, furthering comprising at least one belt connected to said container body for fastening said container body around a waist section of said user.

11. A fire emergency life saving arrangement, as recited in claim 1, furthering comprising an air filtering room between said second dividing plate and an end wall of said air storage area, wherein said air filtering area contains a filter installed therein and has an air intake opening provided on a wall of said filtering room for allowing air to enter, on said second dividing plate, an air outlet hole being provided for said buffer air room to communicate with said air filtering area, wherein an air outlet valve is used to close said air outlet hole.

12. A fire emergency life saving arrangement, as recited in claim 11, furthering comprising a side cover for detachably covering said air intake opening.

13. A fire emergency life saving arrangement, as recited in claim 4, furthering comprising and air filtering area between said second dividing plate and an end wall of said air storage area, wherein said air filtering area contains a filter installed therein and has an air intake opening provided on a wall of said filtering area for allowing air to enter, on said second dividing plate, an air outlet hole being provided for said buffer air area to communicate with said filtering area, wherein an air outlet valve is used to close said air outlet hole.

14. A fire emergency life saving arrangement, as recited in claim 13, furthering comprising a side cover for detachably covering said air intake opening.

15. A fire emergency life saving arrangement, as recited in claim 5, furthering comprising and air filtering area between said second dividing plate and an end wall of said air storage area, wherein said air filtering area contains a filter installed therein and has an air intake opening provided on a wall of said filtering area for allowing air to enter, on said second dividing plate, an air outlet hole being provided for said buffer air area to communicate with said filtering area, wherein an air outlet valve is used to close said air outlet hole.

16. A fire emergency life saving arrangement, as recited in claim 15, furthering comprising a side cover for detachably covering said air intake opening.

17. A fire emergency life saving arrangement, as recited in claim 7, furthering comprising and air filtering area between said second dividing plate and an end wall of said air storage area, wherein said air filtering area contains a filter installed therein and has an air intake opening provided on a wall of said filtering area for allowing air to enter, on said second dividing plate, an air outlet hole being provided for said buffer air area to communicate with said filtering area, wherein an air outlet valve is used to close said air outlet hole and a side cover is used to detachably cover said air intake opening.

18. A fire emergency life saving arrangement, as recited in claim 8, furthering comprising and air filtering area between said second dividing plate and an end wall of said air storage area, wherein said air filtering area contains a filter installed therein and has an air intake opening provided on a wall of said filtering area for allowing air to enter, on said second dividing plate, an air outlet hole being provided for said buffer air area to communicate with said filtering area, wherein an air outlet valve is used to close said air outlet hole and a side cover is used to detachably cover said air intake opening.

19. A fire emergency life saving arrangement, as recited in claim 9, furthering comprising and air filtering area between said second dividing plate and an end wall of said air storage area, wherein said air filtering area contains a filter installed therein and has an air intake opening provided on a wall of said filtering area for allowing air to enter, on said second dividing plate, an air outlet hole being provided for said buffer air area to communicate with said filtering area, wherein an air outlet valve is used to close said air outlet hole and a side cover is used to detachably cover said air intake opening.

20. A fire emergency life saving arrangement, as recited in claim 10, furthering comprising and air filtering area between said second dividing plate and an end wall of said air storage area, wherein said air filtering area contains a filter installed therein and has an air intake opening provided on a wall of said filtering area for allowing air to enter, on said second dividing plate, an air outlet hole being provided for said buffer air area to communicate with said filtering area, wherein an air outlet valve is used to close said air outlet hole and a side cover is used to detachably cover said air intake opening.

* * * * *